(12) United States Patent
Brown et al.

(10) Patent No.: US 12,296,999 B2
(45) Date of Patent: May 13, 2025

(54) DEVICE FOR REFILLING ELECTRONIC CIGARETTE CARTRIDGE

(71) Applicant: Fontem Ventures B.V., Amsterdam (NL)

(72) Inventors: Steven E. Brown, Oak Ridge, NC (US); Luis A. Sanchez, Greensboro, NC (US)

(73) Assignee: Fontem Ventures B.V., Amsterdam (NL)

( * ) Notice: Subject to any disclaimer, the term of this patent is extended or adjusted under 35 U.S.C. 154(b) by 0 days.

(21) Appl. No.: 17/524,647

(22) Filed: Nov. 11, 2021

(65) Prior Publication Data

US 2022/0242598 A1    Aug. 4, 2022

Related U.S. Application Data

(62) Division of application No. 16/360,364, filed on Mar. 21, 2019, now abandoned, which is a division of
(Continued)

(51) Int. Cl.
*A24F 47/00*    (2020.01)
*B65B 3/10*    (2006.01)
(Continued)

(52) U.S. Cl.
CPC .............. *B65B 3/10* (2013.01); *A24F 15/015* (2020.01); *A24F 40/10* (2020.01); *A24F 40/485* (2020.01);
(Continued)

(58) Field of Classification Search
CPC ...... B65B 3/04; B65B 3/10; A61M 2209/045; A24F 15/015; A24F 40/10; A24F 40/485; A24F 40/85
See application file for complete search history.

(56) References Cited

U.S. PATENT DOCUMENTS 2,667,986 A * 2/1954 Perelson ............... A61J 1/2096
215/307
3,624,755 A * 11/1971 Lambert ................. C02F 1/681
137/614.04
(Continued)

FOREIGN PATENT DOCUMENTS

EP    3143884 A2 *    3/2017    ........... A24F 15/015
GB    921899 A        3/1963
(Continued)

OTHER PUBLICATIONS

Extended European Search Report, dated Jan. 17, 2017, p. 1-15.

*Primary Examiner* — Nicolas A Arnett
(74) *Attorney, Agent, or Firm* — Dykema Gossett PLLC

(57) ABSTRACT

A refill bottle and system for an electronic cigarette. The refill bottle and system can comprise a refill bottle. The refill bottle can comprise a bottle housing, a bottle cavity defined by the bottle housing, and a refill assembly coupled to the bottle housing. The refill assembly can comprise a bottle stopper, a movable assembly, a spring, a filling projection, and a projection opening. The refill assembly can be configured to cover the filling projection and the projection opening when no force is acting upon the refill assembly. The refill system can further comprise an eCig tank comprising a tank side wall, a tank reservoir defined by the tank side wall, and a self-sealing port coupled to the tank side wall.

9 Claims, 11 Drawing Sheets

Related U.S. Application Data application No. 15/153,144, filed on May 12, 2016, now abandoned.

(60) Provisional application No. 62/161,164, filed on May 13, 2015.

(51) Int. Cl.
*A24F 15/015* (2020.01)
*A24F 40/10* (2020.01)
*A24F 40/485* (2020.01)
*A24F 40/85* (2020.01)

(52) U.S. Cl.
CPC ........ *A24F 40/85* (2020.01); *A61M 2209/045* (2013.01)

(56) References Cited

U.S. PATENT DOCUMENTS

| | | | | |
|---|---|---|---|---|
| 3,984,034 | A * | 10/1976 | Cohen | B65D 83/64 222/389 |
| 5,249,611 | A * | 10/1993 | Law | B67D 3/04 141/335 |
| 5,492,147 | A * | 2/1996 | Challender | F16L 37/28 604/905 |
| 5,628,344 | A * | 5/1997 | Roberts | F16L 37/30 137/895 |
| 8,603,051 | B2 * | 12/2013 | Kuo | A61M 5/168 604/288.01 |
| 8,647,310 | B2 * | 2/2014 | Fangrow, Jr. | A61M 39/26 604/236 |
| 8,757,169 | B2 * | 6/2014 | Gysland | A24F 40/00 131/270 |
| 9,308,336 | B2 * | 4/2016 | Newton | A24F 40/485 |
| 9,497,993 | B2 * | 11/2016 | Vallar | A24B 15/00 |
| 9,872,518 | B2 * | 1/2018 | Hearn | A61M 15/06 |
| 10,440,991 | B2 * | 10/2019 | Levitz | F16K 1/221 |
| 2001/0045231 | A1 * | 11/2001 | Monod | F16K 27/067 137/454.2 |
| 2004/0025968 | A1 * | 2/2004 | Allen | B67D 7/005 141/351 |
| 2007/0137649 | A1 * | 6/2007 | Matsumoto | B65D 83/54 128/200.14 |
| 2007/0277902 | A1 * | 12/2007 | Dieudonat | B65D 47/248 141/319 |
| 2012/0104020 | A1 * | 5/2012 | Cur | B67D 1/0001 222/105 |
| 2012/0167906 | A1 * | 7/2012 | Gysland | A24F 40/00 131/328 |
| 2012/0255647 | A1 * | 10/2012 | Dumont | B05B 11/0056 141/311 R |
| 2014/0076310 | A1 * | 3/2014 | Newton | A61M 15/06 128/202.21 |
| 2014/0102584 | A1 * | 4/2014 | Lasnier | B67D 7/0294 141/18 |
| 2014/0283855 | A1 * | 9/2014 | Hawes | A24F 40/48 131/328 |
| 2014/0283946 | A1 * | 9/2014 | Kribs | B65D 47/06 141/2 |
| 2015/0245654 | A1 * | 9/2015 | Memari | H02J 7/0042 141/2 |
| 2015/0282529 | A1 * | 10/2015 | Li | A61M 11/042 131/273 |
| 2015/0282530 | A1 * | 10/2015 | Johnson | A24F 40/485 392/394 |
| 2016/0128384 | A1 * | 5/2016 | Luciani | A24F 40/485 215/44 |
| 2016/0332754 | A1 * | 11/2016 | Brown | B65B 3/10 |
| 2019/0276167 | A1 * | 9/2019 | Brown | B65B 3/10 |

FOREIGN PATENT DOCUMENTS

| | | | | |
|---|---|---|---|---|
| WO | 2010073018 | A1 | 7/2010 | |
| WO | WO-2014195859 | A2 * | 12/2014 | ........ A24F 40/485 |
| WO | 2016/128719 | A1 | 8/2016 | |

\* cited by examiner

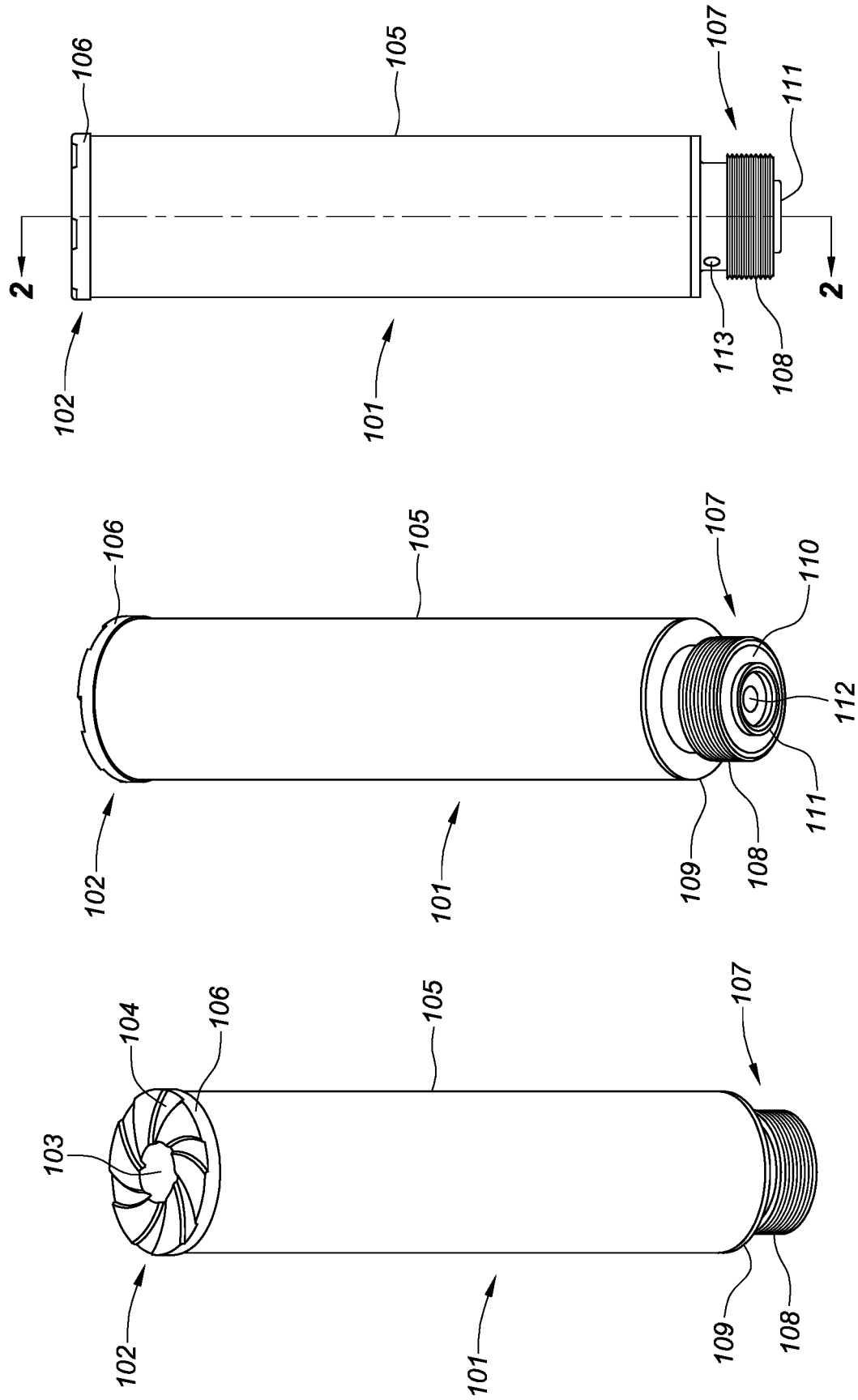

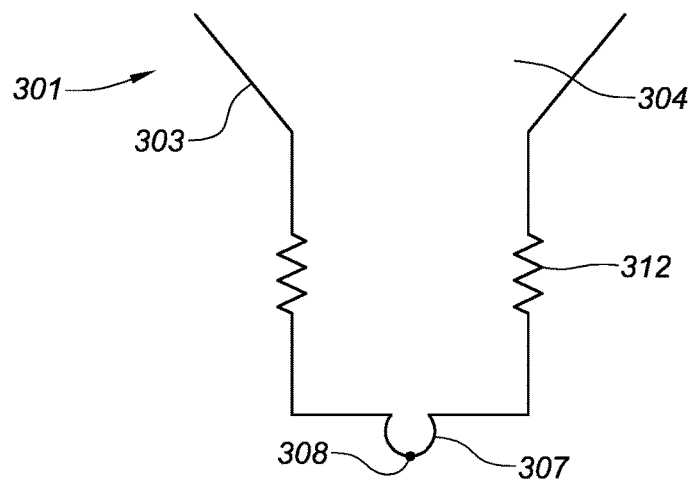
FIG. 7A
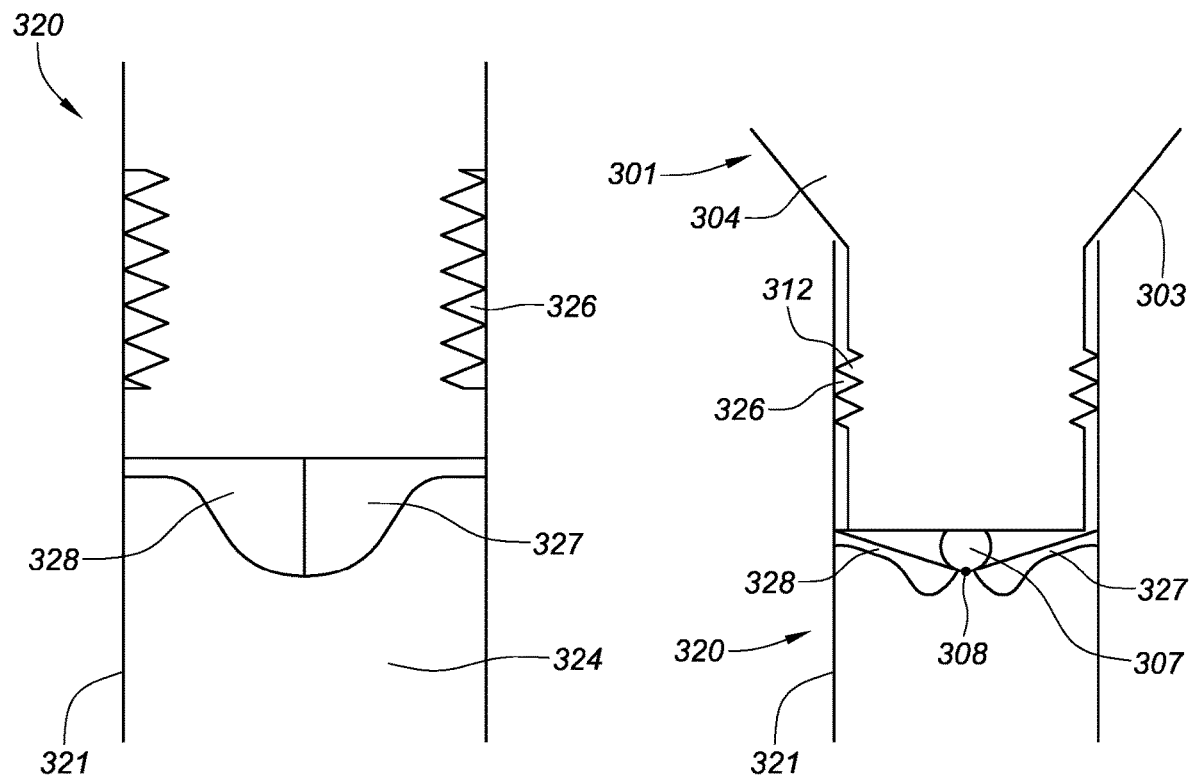
FIG. 7B  FIG. 7C

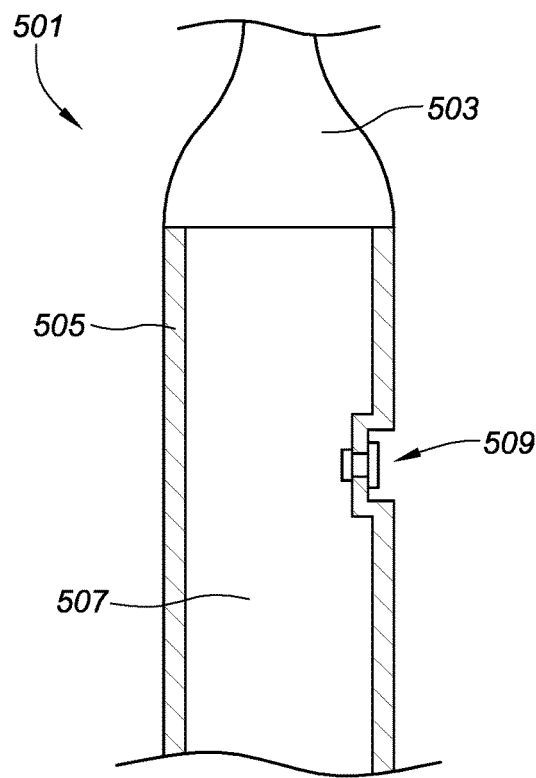 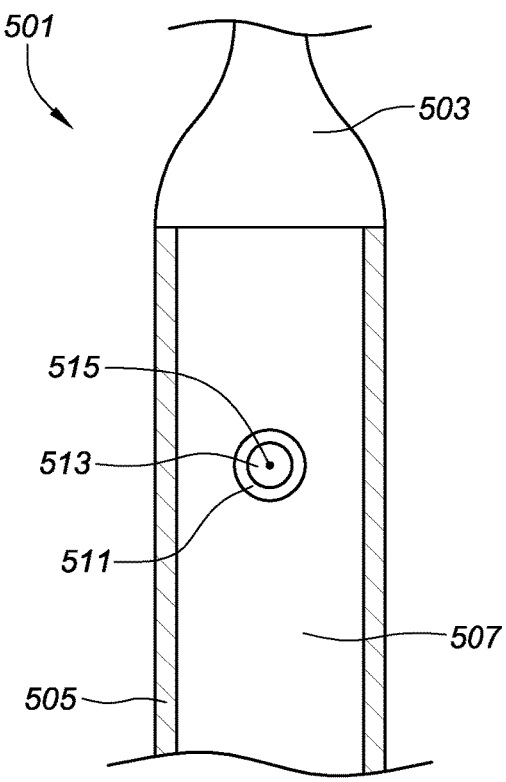
FIG. 9A         FIG.9B
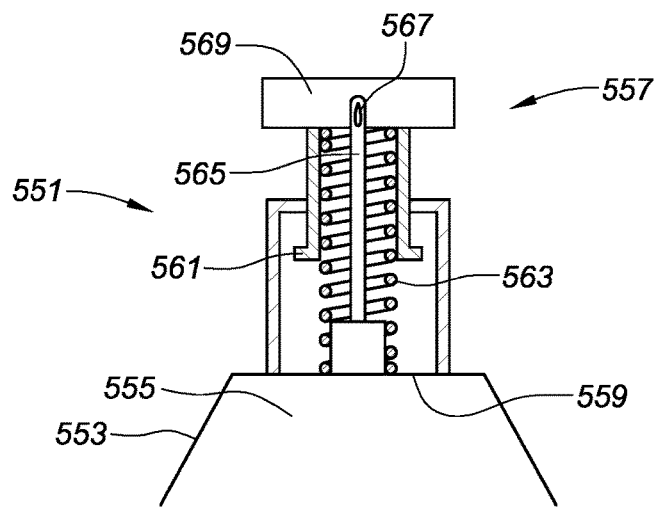
FIG. 10

DEVICE FOR REFILLING ELECTRONIC CIGARETTE CARTRIDGE

CROSS-REFERENCE TO RELATED APPLICATIONS

This application is a division of U.S. application Ser. No. 16/360,364, filed 21 Mar. 2019 (the '364 application), which is a division of U.S. application Ser. No. 15/153,144, filed 12 May 2016 (the '144 application), which claims the benefit of U.S. provisional application No. 62/161,164, filed 13 May 2015, (the '164 application). The '364 application, the '144 application, and the '164 application are all hereby incorporated by reference in their entirety as though fully set forth herein.

BACKGROUND a. Field of the Disclosure

The present invention relates generally to electronic smoking devices and in particular electronic cigarettes. More specifically the present invention relates to filling systems for refilling the reservoir of an electronic smoking device with liquid for vaporization.

b. Background Art

Electronic cigarettes are a popular alternative to traditional smoking articles that burn tobacco products to generate mainstream smoke for inhalation. Unlike traditional tobacco-based smoking articles, electronic cigarettes generate an aerosol-based vapor for inhalation, which can generally emulate mainstream smoke of traditional tobacco based smoking articles.

BRIEF SUMMARY

In one embodiment, a refill bottle for a liquid transferring system can comprise a bottle housing, a bottle cavity defined by the bottle housing, and a refill assembly coupled to the bottle housing. The refill assembly can comprise a bottle stopper, a movable assembly, a spring, a filling projection, and a projection opening. The refill assembly can be configured to cover the filling projection and the projection opening when no force is acting upon the refill assembly. The movable assembly can be configured to be displaced towards the bottle stopper when a force is placed on the movable assembly in a direction of the bottle stopper. The filling projection and the projection opening can be configured to be at least partially uncovered by the refill assembly when a force is placed on the movable assembly in a direction of the bottle stopper.

In another embodiment, a refill system for an electronic cigarette can comprise a refill bottle. The refill bottle can comprise a bottle housing, a bottle cavity defined by the bottle housing, and a refill assembly coupled to the bottle housing. The refill assembly can comprise a bottle stopper, a movable assembly, a spring, a filling projection, and a projection opening. The refill assembly can be configured to cover the filling projection and the projection opening when no force is acting upon the refill assembly. The refill system can further comprise an eCig (electronic cigarette) tank comprising a tank side wall, a tank reservoir defined by the tank side wall, and a self-sealing port coupled to the tank side wall.

In yet another embodiment, a refill system for an electronic cigarette can comprise a refill bottle comprising a bottle housing, a bottle cavity defined by the bottle housing, and a refill assembly coupled to the bottle housing. The refill assembly can comprise a refill check valve and at least one flange. The refill system can further comprise an eCig tank comprising a tank side wall, a tank reservoir defined by the tank side wall, and a self-sealing port coupled to the tank side wall. The self-sealing port can comprise a locking interface, a fill port, and a tank check valve

BRIEF DESCRIPTION OF THE DRAWINGS

FIG. 1A is an isometric top and side view of a device for storing and vaporizing liquid media, in accordance with embodiments of the present disclosure.

FIG. 1B is an isometric bottom and side view of the device in FIG. 1A, in accordance with embodiments of the present disclosure.

FIG. 1C is a side-view of the device in FIG. 1A, in accordance with embodiments of the present disclosure.

FIGS. 7A-7C are partial cross-sectional views of another embodiment of a refill bottle according to the disclosure interacting with another embodiment of an eCig tank according to the disclosure.

FIGS. 9A and 9B are a side view and a top view of another embodiment of an eCig tank according to the disclosure.

FIG. 10 is a cross-sectional view of an embodiment of a refill bottle that can interact with the eCig tank of FIGS. 9A and 9B to refill the eCig tank.

DETAILED DESCRIPTION

Figure 1D:
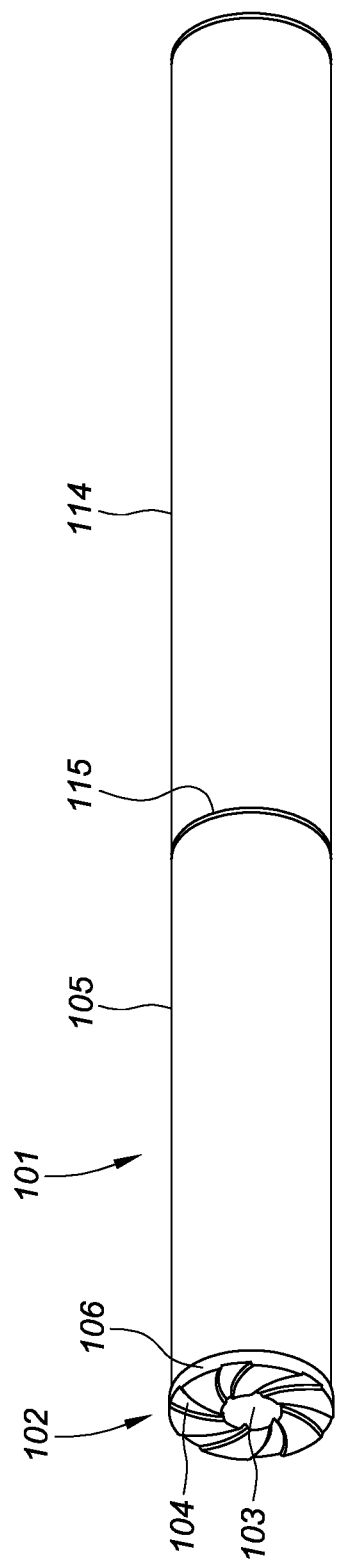
FIG. 1D is an isometric top and side view of an electronic cigarette, in accordance with embodiments of the present disclosure.

Referring now to the drawings wherein like reference numerals are used to identify identical components in the various views, FIG. 1A is an isometric top and side view of a device 101 for storing and vaporizing liquid media, in accordance with embodiments of the present disclosure. In an example, the device 101 can be a cartomizer for an electronic cigarette, which can be connected with a power source (e.g., battery) to provide power for an atomizer contained within the device 101. The device 101 can include a mouth piece 102 with an outlet 103, which can be configured for delivery of a vapor to a user.

The mouth piece 102 can be sized and configured to provide a user with a particular type of experience. For instance, adjusting a size and/or shape of the outlet 103 and/or a passageway within the mouthpiece, shown in FIG. 3, can result in a change in velocity of vapor exiting the outlet 103 and/or a change in particle size of the liquid media contained in the vapor. As such, a different user experience can be associated with the change in velocity and/or particle size. For example, the vapor exiting the outlet 103 may feel different to a user when it enters their mouth, as a result of the change in velocity and/or particle size. In some examples, the mouth piece 102 can comprise a pattern 104, which can be associated with a particular user experience associated with the mouth piece 102 and/or device 101. The pattern 104 can be used by a user to identify the particular user experience associated with the mouth piece 102 and/or device 101.

The device 101 can include an outer tube 105 that is connected with the mouth piece 102. In an example, the mouth piece 102 can be connected with the outer tube 105 by press-fitting the mouth piece 102 into the outer tube 105 and/or through use of an adhesive applied between the outer tube 105 and the mouth piece 102, although other connecting technologies may be used. In some embodiments, the mouth piece 102, as well as other components of the device 101, can be connected with the outer tube 105 via a snap connecter, as discussed herein. The mouth piece 102 can include a stepped portion 106 (or annular ledge) that can engage the proximal longitudinal end of the outer tube 105 to prevent the mouth piece 102 from being pushed into the outer tube further than a defined amount.

The device 101 can include a battery connector 107 (e.g., a threaded connector as shown or a frictionally-engaged connector or other connector) that is configured to connect with a complementary connector comprising part of or associated with a housing for a battery or other power source that is capable of providing power to an atomizer comprising part of the device 101. In an example, the battery connector 107 can be connected with the outer tube 105 by press-fitting the battery connector 107 into the outer tube 105 and/or, for example, through use of an adhesive applied between the outer tube 105 and the battery connector 107. The battery connector 107 can include a stepped portion 109 (or annular ledge), much like the mouth piece 102 that can engage the distal longitudinal end of the outer tube 105 to prevent the battery connector 107 from being pushed into the outer tube 105 further than a defined amount.

The battery connector 107 can establish both a physical connection between the device 101 and a housing for a power source and an electrical connection between the power source (e.g., the battery in the housing) and the device 101. In an example, the physical connection can be established by a first threaded portion 108, which can be configured to threadingly connect with a complimentary threaded portion associated with the battery. The first threaded portion 108 of the connector 107 can be constructed from an electrically conductive material (e.g., metal). The connector 107 may further comprise, for example, a center connector 111, which may also be constructed from an electrically conductive material. As discussed further below, the first threaded portion 109 and the center connector 111 may be electrically insulated from each other by an annular insulator grommet 110. Thus, the connector 107, via the first threaded portion 108 and the center connector 111, can facilitate an electrical connection between a first terminal (e.g., positive terminal) and a second terminal (e.g., negative terminal) of the battery.

FIG. 1B is an isometric bottom and side view of the device 101 in FIG. 1A, in accordance with embodiments of the present disclosure. The device 101 includes the mouth piece 102, the stepped portion 106 of the mouth piece 102, the outer tube 105, the battery connector 107, the threaded portion 108 of the battery connector 107, and the stepped portion 109 of the battery connector 107. FIG. 1B further illustrates details associated with the battery connector 107, which can include an annular insulator grommet 110 that is inserted into an axial cylindrical opening of the battery connector 107. The annular insulator grommet 110 can include an axial cylindrical opening, in which a center battery connect 111 can be inserted. The annular insulator grommet 110 can be formed from an insulative material that separates the center battery connect 111 from the threaded portion 108 and/or stepped portion 109. For example, the annular insulator grommet 110 can be formed of a plastic, rubber, ceramic, etc., which can prevent a short from occurring between the center battery connect 111 and the threaded portion 108 and/or stepped portion 109.

In some embodiments, the center battery connect 111 can include an axial cylindrical opening 112 in the center battery connect 111 that is in communication with the inner surface of the inner tube 118. In an example, a first terminal of the battery can be connected with the threaded portion 108 and/or stepped portion 109 and a second terminal of the battery can be connected with the center battery connect 111. For instance, a positive terminal of the battery can connect to the threaded portion 108 and/or stepped portion 109 and a negative terminal of the battery can connect to the center battery connect 111.

FIG. 1C is a side-view of the device 101 in FIG. 1A, in accordance with embodiments of the present disclosure. The device 101 includes the mouth piece 102 with stepped portion 106. The mouth piece 102 can be connected with the outer tube 105 and can include stepped portion 106. In addition, the device 101 can include battery connector 107 that has a threaded portion 108 and stepped portion 109. The battery connector 107 can include an axial cylindrical opening in which an insulator grommet 110 (as shown in FIG. 1B) can be inserted to provide an insulative layer between a center battery connect 111 inserted in an axial cylindrical opening of the insulator grommet 110 and the threaded portion 108 of the battery connector 107. In addition, the device 101 can include an air inlet 113 through which air can be drawn into the device 101. In some embodiments, the device 101 can include more than one air inlet 113. For example, air can be drawn through an axial cylindrical opening of the center battery connect 111.

FIG. 1D is an isometric top and side view of an electronic cigarette, in accordance with embodiments of the present disclosure. The electronic cigarette includes a device 101 that is connected with a battery assembly 114. The battery assembly 114 can include a power source (e.g., battery) that is used to power a heater coil housed in the device 101, as discussed herein. The connection between the device 101 and the battery assembly 114 can be a threaded connection and/or a frictionally-engaged connection or other type of connection that is configured to connect the device 101 and the battery assembly 114. In an example, the threaded connection can include a first threaded portion on the device 101 and a complimentary threaded portion on the battery assembly 114. The frictionally-engaged connection can include two complementary connectors that are configured to frictionally engage one another, as discussed herein. Upon connection of the device 101 and the battery assembly 114, a joint 115 can be formed between the device 101 and the battery assembly 114.

FIG. 1D further depicts the mouth piece 102 of the device 101. The mouth piece 102 includes the outlet 103 where vapor exits the electronic cigarette, as a user draws from the mouth piece 102. As discussed herein, the stepped portion 106 of the mouth piece 102 can engage the proximal end of the outer tube 105, thus preventing the mouth piece 102 from being pushed into the outer tube 105 further than a defined amount. In addition, the mouth piece 102 can comprise the pattern 104, such that a user can identify the particular user experience associated with the mouth piece 102 and/or device 101.

In some embodiments, the battery assembly 114 can include a light assembly 116 on a tip of the battery assembly 114 distal to the device 101. The light assembly 116 can include a light filter and a light emitting diode (LED). As a user draws on the mouth piece 102, the LED can generate light which passes through the light filter. In an example, the light filter can disperse the light generated by the LED and/or can impart a particular color to the light generated by the LED.

Figure 2:
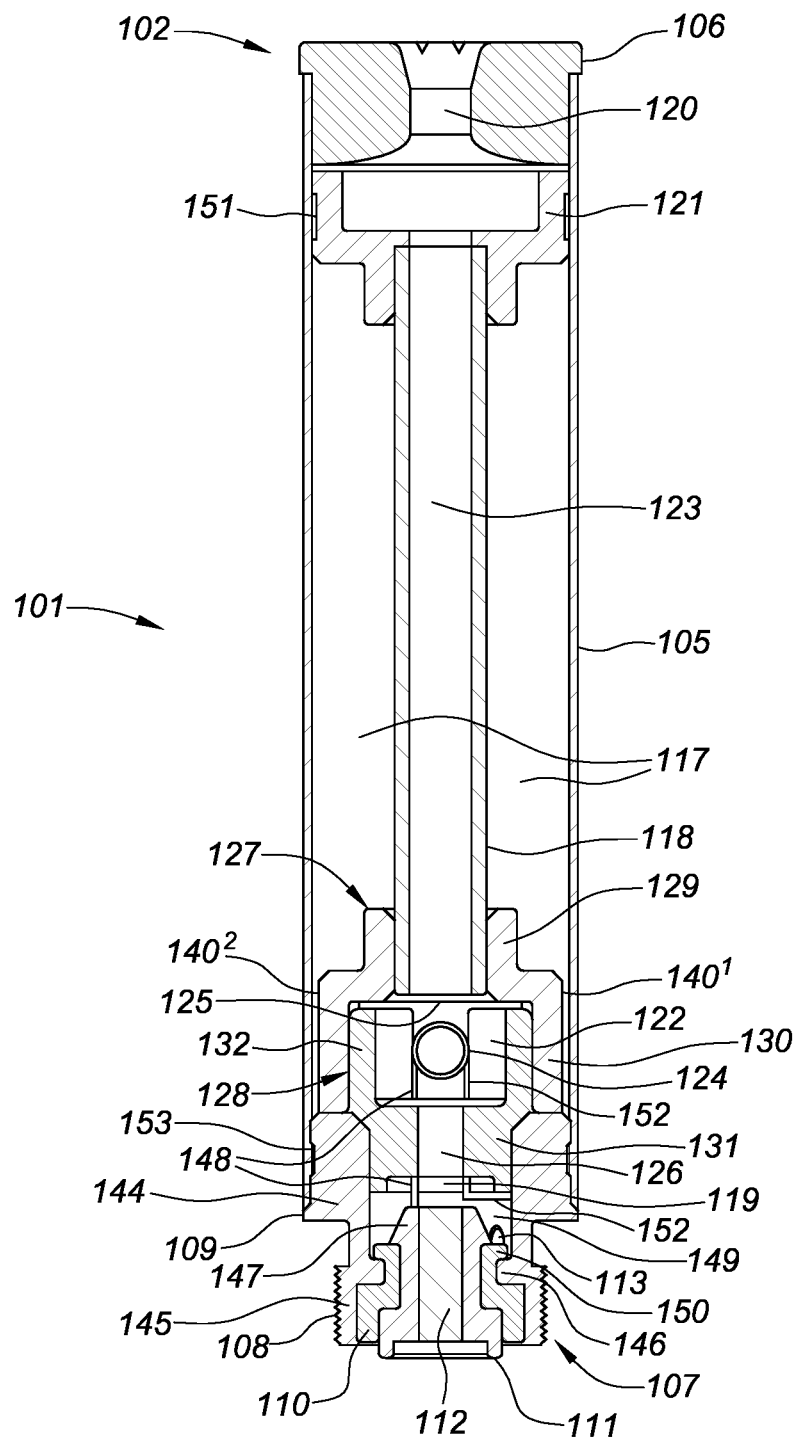
FIG. 2 is a cross-sectional view of the device of FIG. 1C taken along line 2-2, in accordance with embodiments of the present disclosure.

FIG. 2 is a cross-sectioned view of the device 101 of FIG. 1C taken along line 2-2, in accordance with embodiments of the present disclosure. The device 101 can include a liquid media storage tank 117 that can be configured to hold a liquid media. In an example, the liquid media can include a smoking liquid that can be vaporized by an atomizer and inhaled by a user. The liquid media can include a flavoring and/or nicotine to enhance a user's experience. The liquid media storage tank 117 can be annular in shape and can be defined by an outer surface of an inner tube 118 and an inner surface of an outer tube 105.

In some embodiments, the inner tube 118 and/or the outer tube 105 can be annular in shape. The inner tube 118 and the outer tube 105 can be connected with a mouth piece 102, in some embodiments. As such, vapor can travel through an air path 123 defined by an inner surface of the inner tube 118 through a passageway 120 formed in the mouth piece 102. In addition, by connecting the outer tube 105 to the mouth piece 102, a proximal end of the liquid media storage tank 117 can be sealed by a connection between the outer tube 105 and the mouth piece 102 and a connection between the inner tube 118 and the mouth piece 102. Alternatively, in some embodiments, a proximal seal 121 can be placed between the inner tube 118 and the mouth piece 102, as illustrated in FIG. 2. In an example, the proximal seal 121 can have an outer surface that connects with an inner surface of the outer tube 105 and can have an inner surface that connects with an outer surface of the inner tube 118, thus sealing the proximal end of the liquid storage media tank 117.

In some embodiments, the proximal seal 121 and the outer tube 105, and/or other portions of the device 101 (e.g., mouth piece 102 and outer tube 105, inner tube 118 and proximal seal 121, heater coil housing 127 and heater coil support 128, outer tube 105 and battery connector 107, etc.) can be connected via snap connectors 151, 153. The snap connectors 151, 153 can include a lip portion and a corresponding recessed portion that engage one another. In an illustrative example, when the proximal seal 121 has been inserted into the outer tube 105 an appropriate amount, the lip portion and the corresponding recessed portion can engage one another, as discussed further in relation to FIG. 4.

Alternatively, and/or in addition, elements 151, 153 can represent seals. In an example, the upper seal 121 and/or battery connector can have an annular groove extending around an outer perimeter between an inside of the outer tube and the upper seal 121 and/or between the inside of the outer tube and the upper seal 121. Each groove can have a proximal wall and a distal wall and material between the proximal wall and the distal wall can be removed to form the groove. In some examples, a seal can be placed in the grooves between the proximal wall and distal wall. For instance, an annular seal can be placed in the grooves and when the upper seal 121 and/or the battery connector 107 is inserted into the outer tube, the seal can be deformed and compressed between the battery connector 107 and the outer tube 105 and the upper seal 121 and the outer tube 105. Thus, a seal can be created between the battery connector 107 and the outer tube 105 and/or between the upper seal 121 and the outer tube 105.

In some embodiments, a distal end of the inner tube 118 can be connected with a chamber air outlet 125 of a heater coil chamber 122. The heater coil chamber 122 can include a chamber that houses a heater coil 124, a chamber air inlet 126, and the chamber air outlet 125. In an example, the heater coil 124 can vaporize liquid media drawn from liquid media storage tank 117, which can be mixed in the heater coil chamber 122 with air received from the chamber air inlet 126. The mixture of vapor and air can then be drawn through the chamber air outlet 125, through the inner tube 118 and passageway 120 of the mouth piece 102.

The heater coil chamber 122 can be formed by a heater coil housing 127 that includes the chamber air outlet 125 and a heater coil support 128 that includes the chamber air inlet 126. Together, the heater coil housing 127 and the chamber coil support 128 can form the heater coil chamber 122. The heater coil housing 127 can be annular in shape and can include a neck portion 129 and a base portion 130. The neck portion 129 can have an inner diameter that is less than an inner diameter of the base portion 130 and can be configured to receive the distal end of the inner tube 118. Forming the inner tube 118 and the heater coil housing 127 as separate components can be advantageous when different lengths of the device 101 are produced. For example, in contrast to prior methods that form the inner tube and heater coil housing/heater coil chamber from one piece, if various sizes of electronic cigarettes are produced, a longer/shorter inner tube 118 may be used, rather than producing a new one piece assembly that includes a heater coil housing and an inner tube of a different length.

The heater coil support 128 can be annular in shape and can include a neck portion 131 and a base portion 132. In some embodiments, an outer diameter of the base portion 132 of the heater coil support 128 can be less than an inner diameter of the base portion 130 of the heater coil housing 127. The base portion 132 of the heater coil support 128 can be inserted into the base portion 130 of the heater coil housing 127 and connected with the base portion 130 of the heater coil housing 127. The heater coil housing 127 and the heater coil support 128 define the heater coil chamber 122 between the chamber air inlet 126 and the chamber air outlet 125.

Some embodiments of the present disclosure can include a removable flavoring pack. In an example, juice can be included in the liquid media storage tank 117, which contains nicotine. Flavoring can be contained in a separate pack that can be attached to the device 101. As such, when a user draws from the device 101, flavoring can be introduced into the air path that travels through the device. In some examples, the mouth piece 102 can be detachable and a flavor pack can be inserted upstream (distal) from the mouth piece 102. In an example, a flavor pack can be inserted between the battery connector 107 and the battery assembly.

In some embodiments, the flavoring pack can include electrical contacts on either end of the flavoring pack that connect the coil 124 to the battery assembly. The flavoring pack can include an electrical lead that connects the center battery connect 111 to a corresponding terminal of the battery assembly. In addition, the flavoring pack can include an additional electrical lead that connects the neck portion 145 of the battery connector 107 to a corresponding terminal of the battery assembly.

In some embodiments, the flavoring pack can include a hole that passes longitudinally through the flavoring pack and connects the axial cylindrical opening 112 to a corresponding axial cylindrical opening of the battery assembly. An annular flavoring tank can surround the hole that passes longitudinally through the flavoring pack, and can be formed by an inner and outer cylindrical wall. In some embodiments, the flavoring pack can contain one or more orifices passing through the inner cylindrical wall, such that flavoring juice can pass from the annular tank and into the hole that passes longitudinally through the flavoring pack. In an example, as a user draws on the device 101, a pressure differential can be created between an interior portion of the annular tank and the hole that passes longitudinally through the flavoring pack. Thus, flavoring juice can be drawn from the flavoring pack into the hole and travel proximally through the device and be inhaled by the user.

In some embodiments, media can be placed in the hole of the flavor pack that absorbs the flavoring, as the flavoring is drawn from the tank through the orifices. In an example, the media can be a cotton like media and/or a porous media. As air passes over the media that contains the absorbed flavoring, the flavoring can be evaporated. In some embodiments, the media can increase a rate at which the flavoring juice evaporates and is introduced into the air path of the device 101. For example, as the flavoring juice is absorbed by the media, a surface area of the flavoring juice exposed to air passing through the media can be increased, thus increasing a rate at which the flavoring juice evaporates.

In some embodiments, the flavoring pack can include a separate wick and heater coil. For instance, the electrical leads in the flavoring pack that connect the coil 124 in the device 101 to the battery assembly can also be connected to a coil located in the longitudinal hole that passes through the flavoring pack. In an example, the coil located in the flavoring pack can be wired in series and/or in parallel with the coil 124 in the device 101. In some embodiments, a wick can extend through an orifice located in the inner cylindrical wall and extend through the wick. The flavoring juice can be pulled from the annular tank along the wick to the coil, where vaporization can occur.

Figure 3:
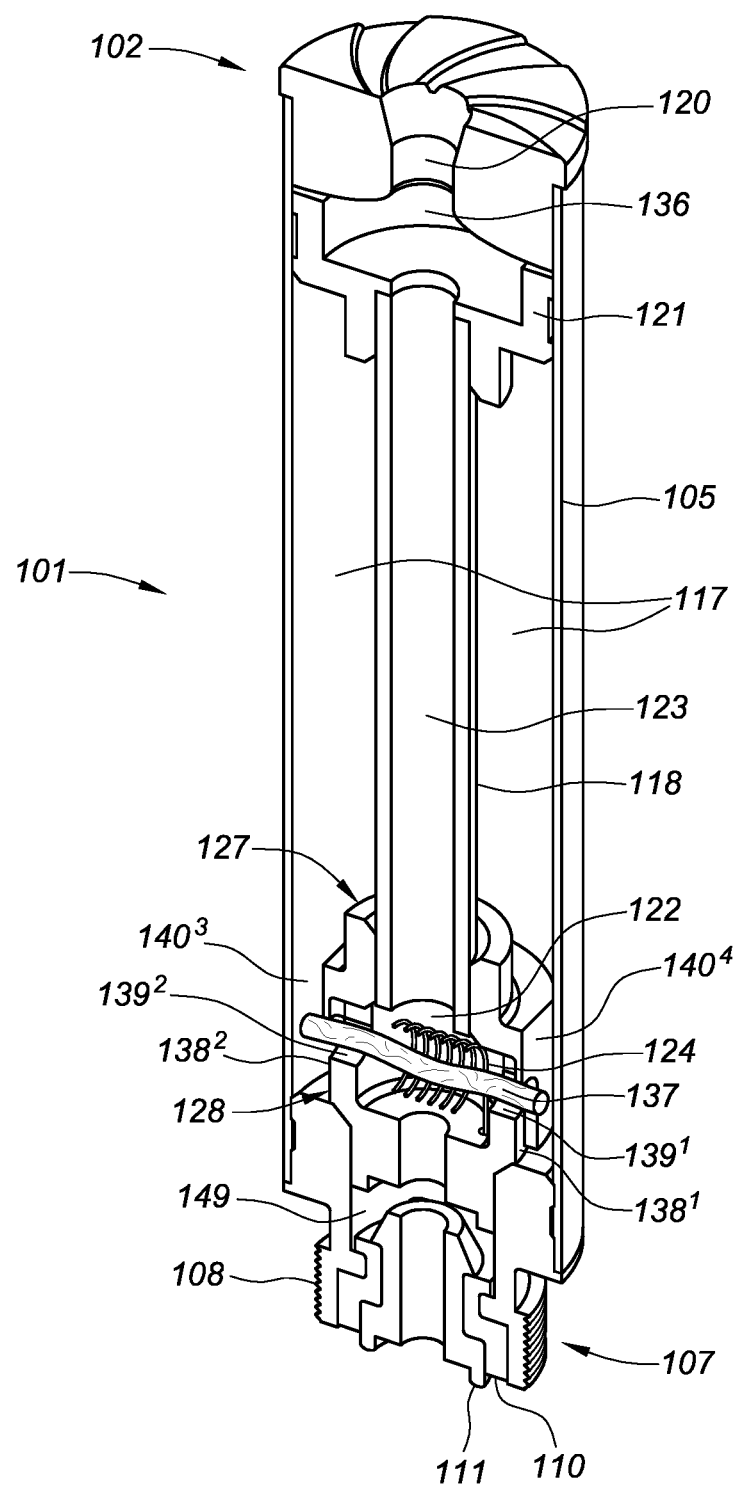
FIG. 3 is an isometric, cross-sectioned view of the top and side of the device depicted in FIG. 2 rotated 90 degrees about a longitudinal axis of the device from the orientation depicted in FIG. 2.

FIG. 3 is an isometric, cross-sectioned view of the top and side of the device 101 depicted in FIG. 2 rotated 90 degrees about a longitudinal axis of the device 101 from the orientation depicted in FIG. 2. The device 101 includes a mouth piece 102 inserted into a proximal end of an outer tube 105. A liquid media storage tank 117 can be included in the device 101 and can be formed by the outer tube 105 and the inner tube 118. In some embodiments, a proximal seal 121 can be placed between the inner tube 118 and the mouth piece 102, as discussed herein, and an outer surface of the proximal seal 121 can connect with an inner surface of the outer tube 105 to create a seal between the liquid media storage tank 117 and the mouth piece 102.

In some embodiments, the proximal seal 121 can include an expansion chamber 136 and the mouth piece 102 can include a passageway 120, through which vapor can flow. In an example, the expansion chamber 136 can have a larger diameter than the inner diameter of the inner tube 118, thus slowing a flow of the vapor to cause turbulence and an increased mixing and/or breaking apart of liquid droplets in the air stream. The vapor can then flow through the passageway 120, which has a smaller inner diameter than the expansion chamber 136, where the flow of the vapor can be sped up, causing additional mixing and/or breaking apart of liquid droplets in the air stream.

In some embodiments, an inner diameter at the distal end of the inner tube 118 can be a same size as an inner diameter at the proximal end of the inner tube 118, resulting in a cylindrical inner surface. Alternatively, in some embodiments, an inner diameter at the distal end of the inner tube 118 can be larger than an inner diameter at the proximal end of the inner tube 118, thus forming a frustoconical shape. In an example, the frustoconical shape of the inner tube 118 can speed up a flow of the vapor through the inner tube 118 before the vapor exits into the expansion chamber 136, in some embodiments. The consecutive speeding up of the flow of the vapor in the inner tube and slowing down of the flow of vapor in the expansion chamber 136 can cause turbulence and thus increased mixing and/or breaking apart of liquid droplets in the air stream.

In an example, such an arrangement can allow for an increased mixing and/or breaking apart of the liquid droplets in the air stream without use of in-stream mixers, while providing a desirable user experience, as opposed to prior methods. For example, some prior methods can have structures that are located in the air stream to change a direction of the flow and/or create turbulence in order to break apart liquid droplets. However, this can cause a restriction in the air path, affecting a user's experience when they draw air through the electronic cigarette. For instance, a user may encounter an increased resistance when drawing air through the electronic cigarette. This can result in a user receiving a less than desired amount of vapor, as opposed to embodiments of the present disclosure, which provide an unrestricted air path 123.

The device 101 can include the heater coil chamber 122 that is formed by the heater coil housing 127 and the heater coil support 128, which houses the heater coil 124. In some embodiments, the heater coil 124 can be disposed horizontally across the heater coil chamber 122, as illustrated in FIG. 3. Alternatively, the heater coil 124 can be disposed vertically within the heater coil chamber 122.

In some embodiments, a wick 137 can extend through a center of the heater coil 124 and through a port in a sidewall of the heater coil chamber 122 into a recessed pocket $140^1$, $140^2$, $140^3$, $140^4$, hereinafter generally referred to as recessed pocket 140, of the liquid media storage tank 117. The wick 137 can extend through a port that extends through the heater coil support 128, and in some cases can extend through the heater coil housing 127. In some examples, one side of the wick 137 can extend through the port in the sidewall of the heater coil chamber 122. Alternatively, a first side of the wick 137 can extend through a first port $139^1$ in the heater coil chamber 122 into a portion of the recessed pocket $140^4$ and a second side of the wick 137 can extend through a second port $139^2$ in the heater coil chamber 122 located on an opposite side of the heater coil chamber from the first port $139^1$ into a portion of the recessed pocket $140^3$.

In some embodiments, the recessed pocket $140^1$, $140^2$, $140^3$, $140^4$ can be formed by an outer surface of the heater coil housing 127 and the inner surface of the outer tube 105. For example, the recessed pocket 140 can be formed by an outer surface of the base portion 130 of the heater coil housing 127 and the inner surface of the outer tube 105, forming an annular recessed pocket 140 around the base portion 130 of the heater coil housing 127.

In an example, the recessed pocket 140 can be configured to retain liquid from the liquid medium storage tank 117, as a result of surface tension. For instance, liquid that enters the recessed pocket 140 can tend to want to remain in the recessed pocket 140, independent of a subsequent orientation of the device 101. Accordingly, a greater amount of liquid in the liquid medium storage tank 117 can be used by the device 101, because remaining liquid, even a small amount, can be retained in the recessed pocket 140 and wicked to the heater coil 124 by the wick 137. In addition, a consistent flow of liquid can be provided to the heater coil 124 by the wick 137 from the liquid medium storage tank 117 up until a point where all, or nearly all of the liquid is used, in contrast to use of a porous material that holds the liquid, as used in prior methods. Because the liquid is free to move about in the liquid media storage tank 117 and does not have to travel through a porous media, which can slow the transfer of the liquid to the wick 137, a consistent amount of liquid can be provided to the wick 137.

In some prior methods that employ a tank to hold the liquid, the liquid may not make consistent contact with the wick, because the liquid is free to move about the tank (e.g., per different orientations of the device 101) and thus may not be drawn consistently to the heater coil via the wick. However, in embodiments of the present disclosure, as discussed herein, the liquid is free to move about the liquid media storage tank 117, but can be retained in the recessed pocket 140, thus ensuring a constant supply of liquid to the heater coil via the wick. The recessed pocket can be sized such that enough liquid is trapped in the recessed pocket 140 to provide liquid for one or more uses (e.g., puffs) by a user. In some examples, after the user removes the device 101 from their mouth after a puff, the orientation of the device 101 can be changed and the recessed pocket 140 can be refilled with liquid from the liquid media storage tank 117, which can subsequently be wicked to the heater coil 124.

In some embodiments, the outer surface of the heater coil housing 127 proximate to the ports $139^1$, $139^2$, can be recessed and/or cut out to form individual recessed pockets $138^1$, $138^2$ for each port $139^1$, $139^2$. In some embodiments, a portion of the heater coil housing 127 bordering the ports $139^1$, $139^2$ can be recessed and/or cut out to form individual recessed pockets $138^1$, $138^2$. For example, as illustrated in FIG. 3, individual recessed pockets $138^1$, $138^2$ can be formed proximate to each port $139^1$, $139^2$, which are further recessed areas in the recessed pocket 140. In an example, where only one port exists, a single recessed pocket can be formed proximate to the port. In some embodiments, the wick 137 can extend through a center of the heater coil 124 through the first port $139^1$ in the heater coil support 128 into a first individual recessed pocket $138^1$ in the liquid media storage tank 117 and through a second port $139^2$ in the heater coil support 128 into a second individual recessed pocket $138^2$ in the liquid media storage tank 117.

In some embodiments, the device 101 can be assembled in a particular way so as to maximize a volume of liquid and reduce an amount of pressure that is developed in the liquid media storage tank 117. In an example, when a pressure in the liquid media storage tank 117 is increased, the increased pressure can force liquid out of the ports $139^1$ and $139^2$, causing liquid to be wasted and also causing possible interference with electronic components as a result of the liquid migrating from the ports $139^1$ and $139^2$ and/or wick 137. As such, it can be desirable to maintain a reduced pressure within the liquid media storage tank 117.

In some embodiments, when assembling the device, the proximal seal and the mouth piece can be inserted first, along with the inner tube 118 and heater coil housing 127. The device 101 can be oriented so the mouth piece 120 points downward and a distal end of the outer tube 105 points upward. In an example, the device can then be filled with liquid to a level that is below a proximal side of the ports $139^1$ and $139^2$. The heater coil support 128, coil 124, wick 137, and battery connector 107 can then be inserted into the distal end of the outer tube 105. Inserting the heater coil support 128, coil 124, wick 137, and battery connector 107 into the distal end of the outer tube 105 can result in a build-up of pressure in the liquid media storage tank 117. However, because the device 101 is placed in an orientation where the ports $139^1$ and $139^2$ remain above a level of the liquid in the liquid media storage tank 117, air can pass through the ports $139^1$ and $139^2$ and out of the device 101 via the axial cylindrical opening 112 and/or the passageway 120 in the mouthpiece 102.

Alternatively, if the device 101 is placed in an orientation where the battery connector 107 points downward and is subsequently filled, liquid can leak from the ports $139^1$ and $139^2$, as the upper seal 121 is set in place. For example, placement of the upper seal can cause an increased pressure in the liquid media storage tank 117, thus causing liquid to be expelled from the ports $139^1$, $139^2$.

With reference to FIG. 2, the device 101 can include a battery connector 107 that comprises an annular outer surface that connects with the inner surface of the outer tube 105 and an annular inner surface configured to connect with an insulator grommet 110 and center battery connect 111. In some embodiments, the battery connector 107 can include a cylindrical base portion 144 and a cylindrical neck portion 145 connected to one another. In some examples, the base portion 144 of the battery connector 107 can be inserted into a distal end of the outer tube 105 a defined amount. For example, the base portion 144 of the battery connector 107 can be inserted into the distal end of the outer tube 105 up until stepped portion 109 makes contact with the outer tube 105. In some embodiments, the battery connector 107 can also be connected with the neck portion 131 of the heater coil support 128. The base portion 144 of the battery connector 107 can include an axial cylindrical with a diameter that is larger than the neck portion 131 of the heater coil support 128. In an example, the diameter of the neck portion 131 of the heater coil support 128 and the diameter of the axial cylindrical opening of the base portion 144 of the battery connector 107 can be such that the neck portion 131 of the heater coil support 128 can be press fit into the base portion 144 of the battery connector 107.

In some embodiments, the battery connector 107 can include a neck portion 145 and an outer surface of the neck portion 145 can include a threaded portion 108 for threading into a battery assembly. The neck portion 145 of the battery connector 107 can include an axial cylindrical opening and a retainer ring 146 disposed around a perimeter of the axial cylindrical opening. An insulator grommet 110 can be inserted into the axial cylindrical opening of the neck portion 145 of the battery connector 107.

In some embodiments, the insulator grommet 110 can be made of an insulative material that is flexible such as a plastic and/or rubber and can be connected with the battery connector 107 via a lip portion 150. In an example, the insulator grommet 110 can be inserted into the axial cylindrical opening in the neck portion 145 of the battery connector 107 and the lip portion 150 can engage the retainer ring 146. The insulator grommet 110 can include an axial cylindrical opening in which a center battery connect 111 can be inserted. The center battery connect 111 can include a lip portion 147 that can engage the insulator grommet 110 to connect the center battery connect 111 to the insulator grommet 110 and to the battery connector 107. The center battery connect 111 can include an axial cylindrical opening 112 through which air can be drawn into the chamber air inlet 126. In an example, the axial cylindrical opening 112 can be in communication with an air path located in the battery assembly connected with the battery connector 107. Air can be drawn through the battery assembly and into the axial cylindrical opening 112.

The insulator grommet 110 can provide an insulative spacer between the center battery connect 111 and the neck portion 145 of the battery connector 107 and the base portion 144 of the battery connector 107. In an example, a first terminal of the battery can electrically connect with the center battery connect 111 and a second terminal of the battery can electrically connect with the neck portion 145 and/or base portion 144 of the battery connector 107 via the threaded portion 108. Power can be provided to the heater coil 124 via a wire 152 connected with a first side of the heater coil 124 and the base portion 144 and/or neck portion 145 of the battery connector 107 and a wire 148 connected with a second side of the heater coil 124 and the center battery connect 111. In an example, as previously discussed, wires 148, 152 can also extend through passageways (not shown) in the neck portion 131 of the heater coil support 128 from the heater coil 124 to the center battery connect 111 and/or to the base portion 144 and/or neck portion 145 of the battery connector 107, thus connecting terminals of the battery to the heater coil 124.

Alternatively, the wires 148, 152 can extend through the chamber air inlet 126. In some embodiments, a wire holder 119 can be provided that can guide the wires 148, 152 from the center battery connect 111 to the heater coil 124. In an example, the wire holder 119 can hold the wires 148, 152 in a center of the passage way and/or in the chamber air inlet 126 such that the wires 148, 152 do not rub on the heater coil support 128, causing a short, for example. In some examples, the heater coil support 128 and/or the heater coil housing 127 can be electrically connected with the base portion 144 and/or the neck portion 145 of the battery connector 107. As such, a wire can extend from the heater coil 124 to the heater coil housing 127 and/or the heater coil support 128 to electrically connect the heater coil 124 to the battery, in some embodiments.

In some embodiments, the battery connector 107 can include an air inlet 113 that can be in communication with an air inlet chamber 149. As a result of a user drawing air through the mouth piece 102, air can be drawn in through the air inlet 113 and into the air inlet chamber 149. The air can be drawn through the chamber air inlet 149 and into the heater coil chamber 122. Liquid that has been wicked into the heater coil 124 via the wick 137 can be heated and vaporized and can be drawn through the air path 123 and passageway 120 into the user's mouth. In some embodiments, the air and vaporized liquid can be drawn into the expansion chamber 136, as discussed herein.

With reference to FIG. 3, the battery connector 107 is shown inserted into the distal end of the outer tube 105 and includes the threaded portion 108, the center battery connect 111, and the insulator grommet 110. In some examples, air can be drawn into the air inlet chamber 149 from an air inlet and an axial cylindrical opening 112 in the center battery connect 111, as shown in FIG. 2, and into the heater coil chamber 122, where liquid can be vaporized by the heater coil 124 and can be drawn through the inner tube 118 into the expansion chamber 136 and through the passageway 120 of the mouth piece 102.

Figure 4:
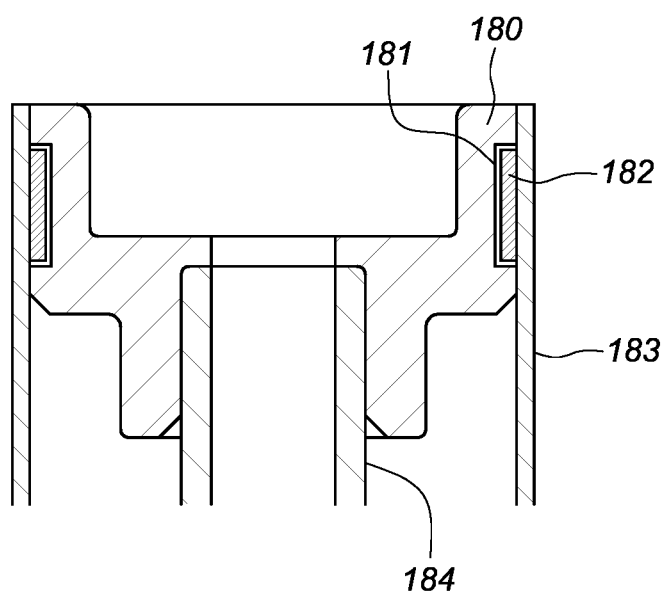
FIG. 4 depicts a connector, in accordance with embodiments of the present disclosure.

FIG. 4 depicts a connector, in accordance with embodiments of the present disclosure. The inner tube 184 is shown as inserted into proximal seal 180, and proximal seal 180 is shown as inserted into outer tube 183 and connected with outer tube 183 via a frictionally engaged connection. In an example, the outer tube 183 has a lip portion 182 and the proximal seal has a corresponding recessed portion 181. As discussed herein, the proximal seal 180 and the outer tube 183, and/or other portions of the device 101 and/or electronic cigarette (e.g., mouth piece 102 and outer tube 105, inner tube 118 and proximal seal 121, heater coil housing 127 and heater coil support, outer tube 105 and battery connector 107, etc., as shown in FIGS. 2 and 3) can be connected via a frictionally engaged connection. The frictionally engaged connection can include a lip portion 182 and a corresponding recessed portion 181 that engage one another when the proximal seal 121 has been inserted into the outer tube 105 an appropriate amount to cause the lip portion 182 and the corresponding recessed portion 181 to engage one another.

In an example, prior methods can use rubber o-rings to create a seal between various portions of an electronic cigarette. For instance, portions that form a tank of an electronic cigarette can be connected and can be sealed via a gasket, such as a rubber o-ring. However, over time, these types of seals can expand and contract, become brittle, and/or can be damaged in an assembly process. Accordingly, embodiments of the present disclosure can provide a frictionally engaged connection that can connect various portions of the device 101, create a seal to prevent liquid from leaking from the tank portion, and aid in assembly of the device 101.

In some embodiments, the various components of the device 101 can be made from a polymer (e.g., plastic), which can provide cost benefits associated with material and manufacturing costs. In an example, use of a semi-elastic polymer can be desirable for use in construction of the frictionally engaged connection, as the polymer components of the device 101 can flex from their original state when one component is being inserted into another and then snap back into their original state when the lip portion 182 is lined up with the corresponding recessed portion 181. For illustration purposes, FIG. 4 illustrates a space between the lip portion 182 and the corresponding recessed portion 181, however, it can be desirable to have little and/or no space between the lip portion 182 and the corresponding recessed portion 181 to maintain a good seal between the various components to prevent liquid from escaping. In addition, having little and/or no space between the lip portion 182 and the corresponding recessed portion 181 can create a stronger connection between various components that the frictionally engaged connection is connecting.

In some embodiments, the frictionally engaged connection can be beneficial when assembling the device 101. For instance, when inserting the proximal seal 180 into the outer tube 183 (or inserting other components into one another), the proximal seal 180 can be inserted into the outer tube 183, until the corresponding recessed portion 181 lines up with the lip portion 182. As such, one component can be inserted into another component a uniform amount between devices, since the separate components are not connected until the corresponding recessed portion 181 lines up with the lip portion 182. In some embodiments, an adhesive can be used in addition to the frictionally engaged connection. In an example, adhesive can be applied to one or both of the components and they can be inserted into one another until the corresponding recessed portion 181 engages the lip portion 182. The frictionally engaged connection can hold the components together while the adhesive cures, in some embodiments.

Figure 5A:
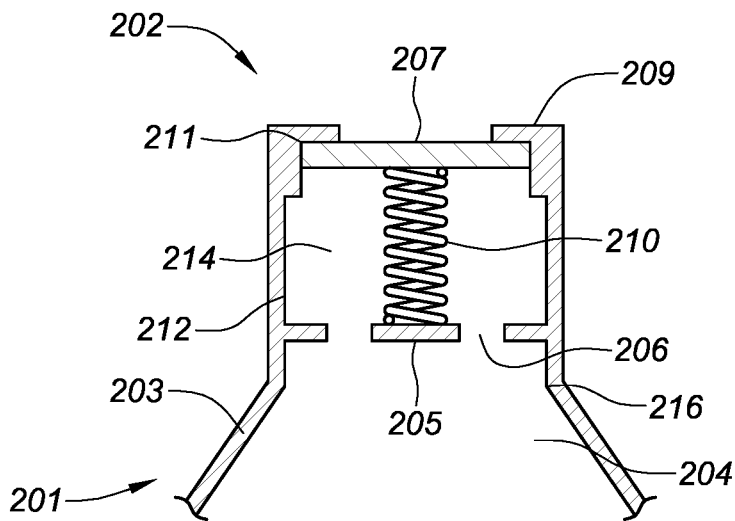
FIG. 5A is a partial cross-sectional view of an embodiment of a refill bottle in accordance with embodiments of the present disclosure.

FIG. 5A illustrates a cross-sectional view of the refill assembly 202 of the refill bottle 201. The refill bottle 201 can comprise a bottle housing 203 that can define a bottle cavity 204. The refill assembly 202 can comprise a lid retainer 209, a movable lid 207, a spring 210, at least one liquid port 206, a port housing 205, a shoulder 211, and an indentation 212. The port housing 205 can comprise at least one liquid port 206. The port housing 205 can be sized and configured to fit within a neck 216 of the bottle housing 203. The at least one liquid port 206 can be shaped in a variety of configurations to allow a liquid to flow through the port housing and into refill cavity 214. The movable lid 207 can be coupled to the spring 210 which can be coupled to the port housing 205. In one embodiment, a structural element can be included inside the spring 210 to assist in retaining the movable lid 207 against the shoulder 211 after the movable lid 207 is moved as will be illustrated in FIGS. 6A and 6B. The movable lid 207 is configured to be pressed against the shoulder 211 of the refill assembly 202 by the spring 210. An indentation 212 can be included within the refill assembly 202 to allow a fluid to flow past the movable lid 207 when the movable lid 207 is moved away from the shoulder 211 of the refill assembly 202.

Figure 5B:
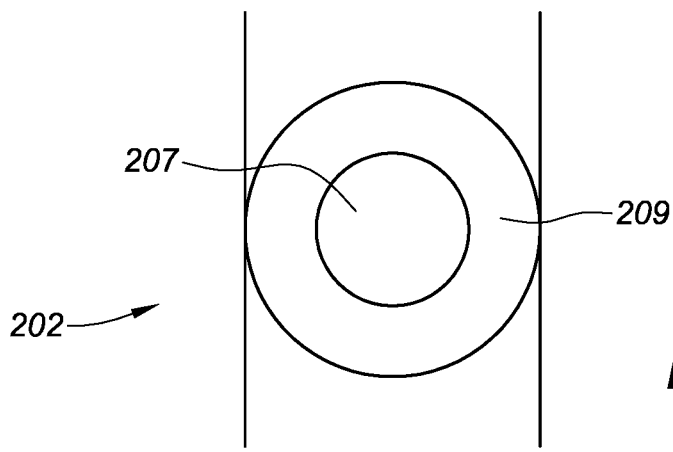
FIG. 5B is a top view of the refill assembly shown in cross section in FIG. 5A.

FIG. 5B illustrates a top view of the refill assembly 202. The movable lid 207 is shown adjacent to the lid retainer 209. In one embodiment the movable lid 207 is configured to rest against the lid retainer 209.

Figure 5C:
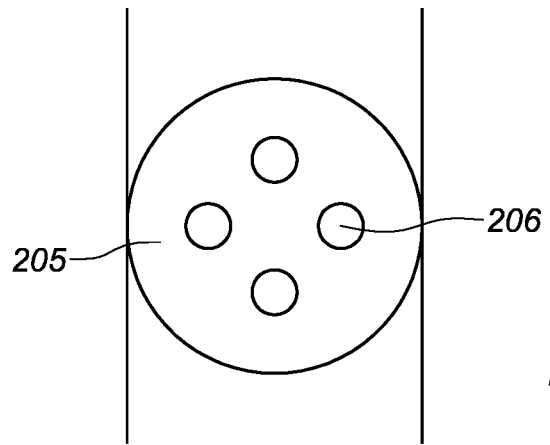
FIG. 5C is a bottom view of the refill assembly shown in cross-section in FIG. 5A.

FIG. 5C illustrates a bottom view of the port housing 205. The port housing 205 can comprise at least one liquid port 206. In the illustrated embodiment the at least one liquid port 206 can comprise four circle extending through the port housing 205. In other embodiments the at least one liquid port 206 can comprise different numbers and different shapes. The at least one liquid port 206 can be configured to allow for fluid to flow from the bottle cavity 204 to the refill cavity 214 as shown in FIG. 5A.

Figure 6A:
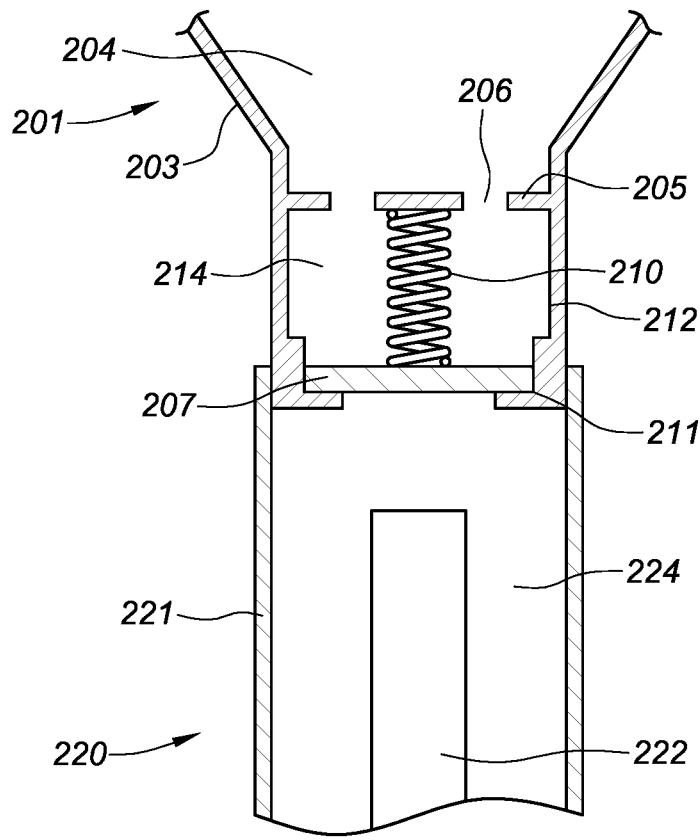
FIGS. 6A and 6B are partial cross-sectional views of an embodiment of a refill bottle according to the disclosure interacting with an embodiment of an eCig tank according to the disclosure.
Figure 6B:
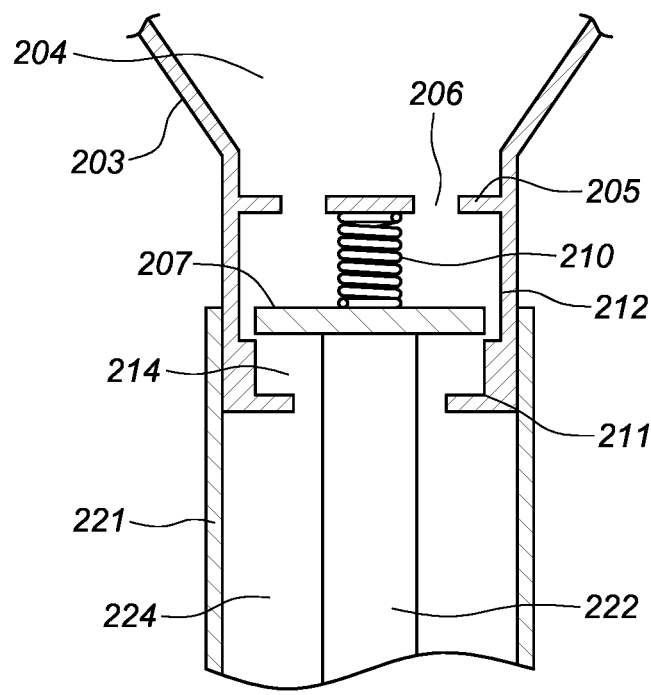

FIGS. 6A and 6B illustrate the refill bottle 201 of FIG. 5A being placed within an eCig tank 220. The eCig tank 220 can comprise a tank housing 221, a vapor tube 222, and a tank cavity 224. The refill bottle 201 can be sized and configured to be placed within the tank housing 221 of the eCig tank 220. The vapor tube 222 can be made of a stiff material. In one embodiment the vapor tube 222 can comprise a metal. In another embodiment the vapor tube 222 can comprise a plastic material. The vapor tube 222 can be sized to interact with the movable lid 207 to depress the movable lid 207 into the refill cavity 214. As seen in FIG. 6B, when the vapor tube 222 interacts with the movable lid 207, a fluid path is opened from the bottle cavity 204 to the tank cavity 224. In the illustrated embodiment a liquid can move from the bottle cavity 204 through the at least one liquid port 206 and the refill cavity 214, past the movable lid 207 and in to the tank cavity 224. When the refill bottle 201 is removed from the eCig tank 220 the movable lid 207 is moved back against the shoulder 211 of the refill assembly 202 by the force of the spring 210. Once the movable lid 207 is placed against the shoulder 211 the refill bottle 201 is sealed and liquid within the bottle cavity 204 is impeded from exiting the refill bottle 201.

In one embodiment the eCig tank can comprise a mouth piece as discussed earlier. The mouth piece can be removably coupled to the tank housing. The mouth piece can be removably coupled to the tank housing by a screw thread, by a friction fit, or other type of connection as discussed herein or would be known to one of ordinary skill in the art. By having a removable mouth piece a user can remove the mouth piece from the tank housing, place a refill bottle according to the disclosure against the vapor tube, and filling the tank cavity with a liquid from the refill bottle. In one embodiment the refill bottle can be configured to dispense a known volume of liquid after the movable lid is activated by the vapor tube. The refill bottle can be configured such that the refill cavity is sized to dispense the desired quantity of liquid and the at least one liquid port closes when the movable lid is moved inwards from the shoulder of the refill assembly. A user can dispense a known quantity of liquid into the tank cavity, remove the refill bottle from the eCig tank and then interact the refill bottle with the eCig tank again to dispense another known volume of liquid. In another embodiment, each of the at least one liquid ports can be covered by a one way valve that allows fluid to flow into the refill cavity from the bottle cavity, but does not allow liquid to move back into the bottle cavity from the refill cavity. In one embodiment the refill bottle can further comprise a bladder within the bottle cavity to hold a liquid. The bladder can allow for liquid to exit the refill bottle without necessitating air to move back into the bladder. In another embodiment, the refill bottle can comprise a mechanism that can press against the bladder and when activated by a user can move a predetermined amount of liquid out of the refill bottle.

FIG. 7A depicts another embodiment of a refill bottle 301 according to the disclosure. The refill bottle 301 can comprise a bottle housing 303, a bottle cavity 304, a bottle screw thread 312, a bottle projection 307, and a dispensing hole 308. The bottle projection 307 can be sized and shaped to interact with a sealing member of an eCig. In the illustrated embodiment, the bottle projection 307 can comprise a rounded projection from the refill bottle 301. In other embodiments the bottle projection 307 can comprise other shapes to interact with a sealing member of an eCig. The dispensing hole 308 can be configured to impede the release of any liquid stored within the bottle cavity 304 when the dispensing hole 308 is situated facing down. However, when the refill bottle 301 is squeezed by a user or pressure is otherwise applied to the liquid stored within the bottle cavity 304 the dispensing hole 308 can allow the liquid to exit the refill bottle 301.

FIG. 7B illustrates an embodiment of an eCig tank 320. The eCig tank 320 can comprise a tank housing 321, a tank screw thread 326, a tank cavity 324, a first sealing member 327, and a second sealing member 328. The first and second sealing members 327, 328 can be configured to interact with the bottle projection 307 illustrated in FIG. 7A. The first and second sealing members 327, 328 can be biased towards a closed configuration when the eCig tank 320 is not interacting with other devices or objects.

As seen in FIGS. 7B and 7C the first and second sealing members 327, 328 can have a sealed configuration, as seen in FIG. 7B, and an open configuration, as seen in FIG. 7C. When in the sealed position, the first and second sealing membrane 327 328 can impede or limit the flow of a liquid within the tank cavity 324 past the sealing members. In other embodiments, the sealing member can comprise a single member that can be configured to interact with a projection or other part of a refill bottle to allow a liquid to be transferred into a tank cavity. In yet another embodiment, the sealing member can comprise a plurality of sealing members that are biased towards a closed configuration and when interacted with a projection or other device of a refill bottle can open to allow a liquid to pass into the tank cavity.

FIG. 7C depicts the refill bottle 301 and the eCig tank 320 of FIGS. 7A and 7B interacting with each other. When the refill bottle 301 is coupled to the eCig tank 320 the bottle projection 307 can interact with the first and second sealing members 327, 328 to allow a liquid stored within the bottle cavity 304 to be transferred to the tank cavity 324. When the refill bottle 301 is removed from the eCig tank 320, the first and second sealing members 327, 328 can move back into the closed position as seen in FIG. 7B and seal the tank cavity 324.

Figure 8A:
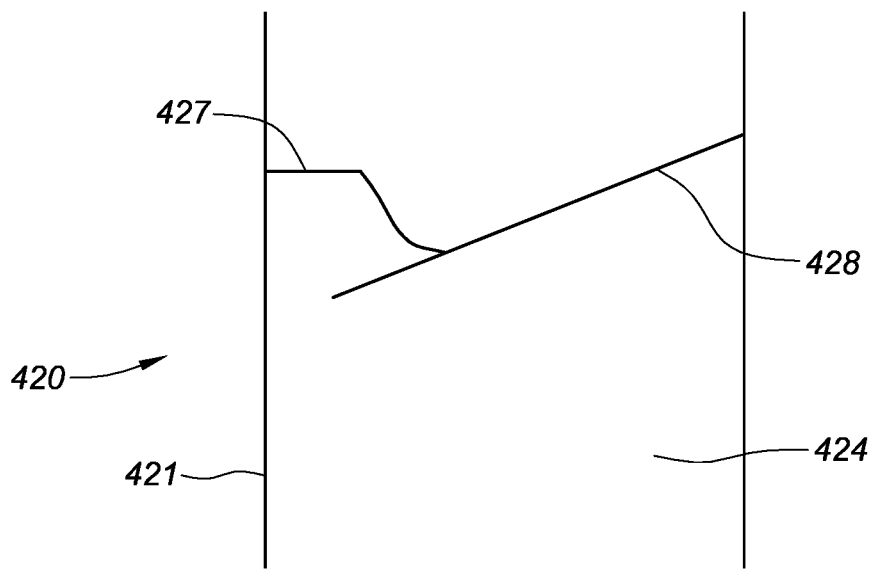
FIGS. 8A and 8B are partial cross-sectional views another embodiment of sealing members of an eCig tank according to the disclosure.
Figure 8B:
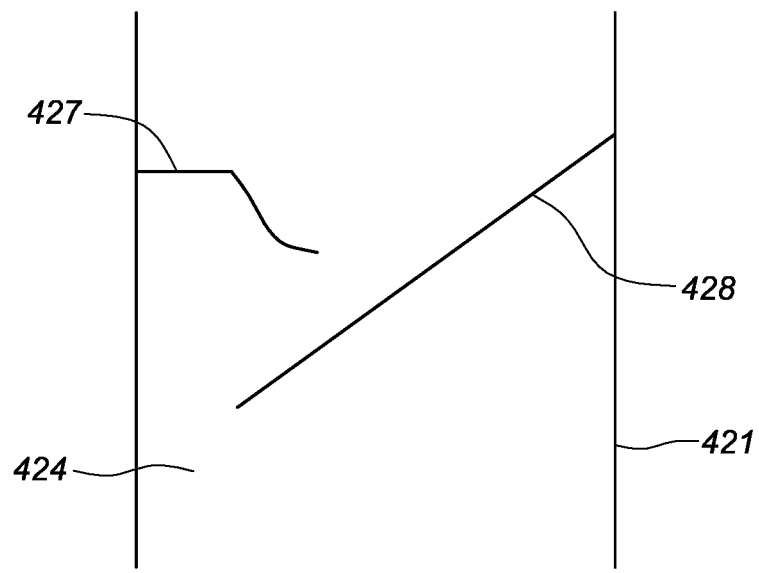

FIG. 8A depicts another embodiment of an eCig tank 420 according to the disclosure. The eCig tank 420 can comprise a tank housing 421, a tank cavity 424, a first sealing member 427 and a second sealing member 428. The first sealing member 427 can be coupled to the tank housing 421 and can extend towards a longitudinal axis of the eCig tank 420. The second sealing member 428 can also be coupled to the tank housing 421 and can extend towards the longitudinal axis of the eCig tank 420. In the illustrated embodiment, the second sealing member 428 can extend distal of the first sealing member 427. The second sealing member 428 can be configured to have a closed position, as illustrated in FIG. 8A, and an open position, as illustrated in FIG. 8B. The second sealing member 428 can be configured to interact with a projection or other component of a refill bottle to move the second sealing member 428 to an open position and facilitate movement of a liquid from a bottle cavity to the tank cavity 424. When the projection or other component of the refill bottle is removed from interacting with the second sealing member 428, the second sealing member 428 can move back to the closed position seen in FIG. 8A and impede or curb the movement of liquid stored in the tank cavity 424 past the first and second sealing members 427, 428

FIGS. 9A and 9B are two views of another embodiment of an eCig tank 501. The eCig tank 501 can comprise a mouth piece 503, a side wall 505, a tank reservoir 507, and a self-sealing port 509. The self-sealing port 509 can be located on the sidewall 505 of the eCig tank 501 and can be configured to mate with a refill bottle as disclosed herein or as would be known to one of ordinary skill in the art. The self-sealing port 509 can comprise a recessed region 511, a self-sealing opening 513, and a self-sealing orifice 515. In one embodiment, the self-sealing orifice 515 can comprise a silicone material. In other embodiments, the recessed region 511 can comprise various shapes to accommodate bottles comprising nozzles of similar shapes and sizes. The self-sealing opening 513 can comprise an opening through the self-sealing port 509 that a projection can be placed through a fluid can be introduced into an interior portion of the eCig tank 501.

FIG. 10 illustrates a cross-sectional view of another embodiment of a refill bottle 551. The refill bottle 551 can comprise a bottle housing 553, a bottle cavity 555, and a refill assembly 557. The refill assembly 557 can comprise a bottle stopper 559, a movable assembly 561, a spring 563, a filling projection 565, a projection opening 567, and a cap 569. The movable assembly 561 can be configured to be displaced towards the bottle stopper 559 when a force is placed on the cap 569 or the movable assembly 561 in the direction of the bottle stopper 559. When the cap 569 and the movable assembly 561 is displaced towards the bottle stopper 559, the filling projection 565 and the projection opening 567 can be uncovered. The projection opening 567 can be in fluid communication with the bottle cavity 555 through the filling projection 565. The spring 563 can be positioned such that once a force is removed from the cap 569 or the movable assembly 561, the movable assembly 561 and the cap 569 can move back into a position to cover the filling projection 565 and the projection opening 567. The cap 569 can be sized and shaped to fit within the recessed region of an eCig tank, such as that illustrated in FIGS. 9A and 9B. A user can place the cap 569 within a recessed region, press the refill bottle against the eCig tank, and move the filling projection 565 and the projection opening 567 into an interior portion of the eCig tank. The user can then transfer a liquid from the refill bottle 551 to the eCig tank. When a desired amount of liquid has been transferred, the user can remove the refill bottle from the eCig tank and the openings into both the eCig tank and the refill bottle will be shut and prevent or minimize any leaks of the liquid within the refill bottle and the eCig tank.

Figure 11A:
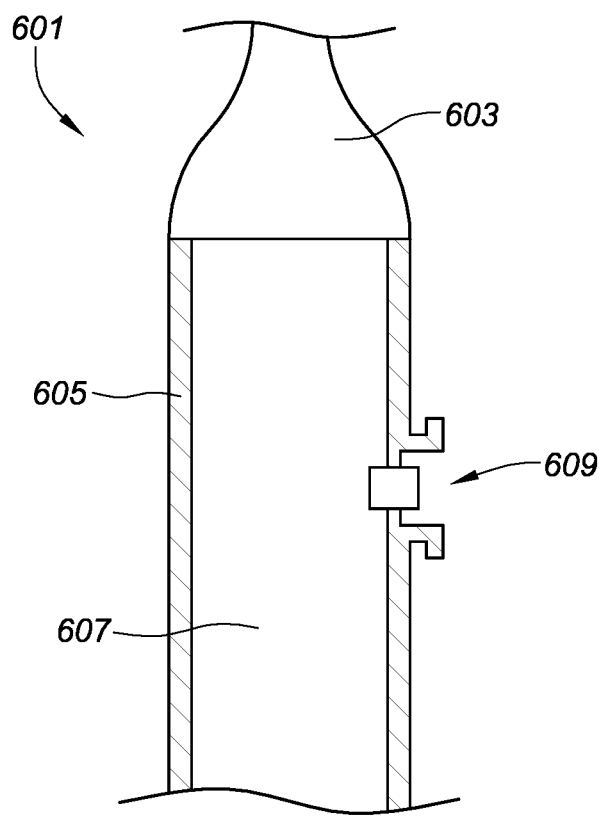
FIGS. 11A and 11B are a side view and a top view of yet another embodiment of an eCig tank according to the disclosure.
Figure 11B:
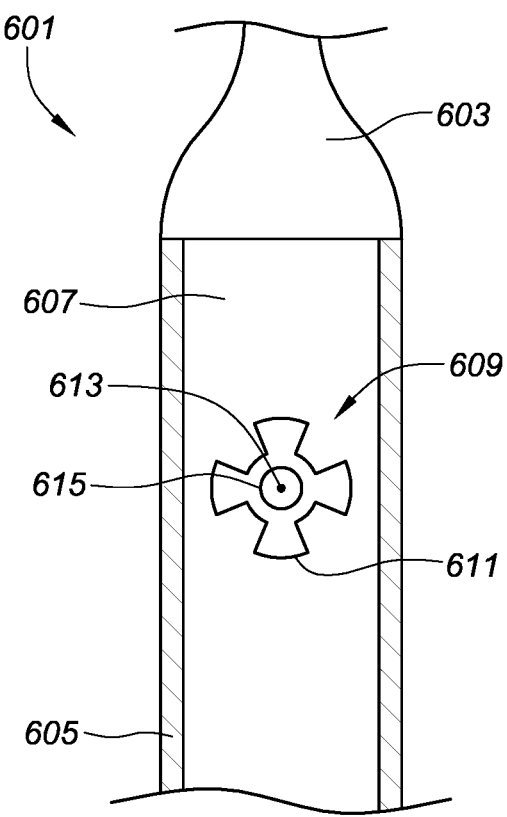

FIGS. 11A and 11B illustrate another embodiment of an eCig tank 601. The eCig tank 601 can comprise a mouth piece 603, a side wall 605, a tank reservoir 607, and a self-sealing port 609. The self-sealing port 609 can be located on the sidewall 605 of the eCig tank 601 and can be configured to mate with a refill bottle as disclosed herein or as would be known to one of ordinary skill in the art. The self-sealing port 609 can comprise a locking interface 611, a fill port 613, and a tank check valve 615. In one embodiment, the self-sealing port 609 can comprise a silicone material. In other embodiments, the recessed region can comprise various shapes to accommodate bottles comprising nozzles of similar shapes and sizes. The tank check valve 615 can comprise an opening through the side wall 605 of the eCig tank 601 and can allow a liquid to flow into the tank reservoir 607.

Figure 12A:
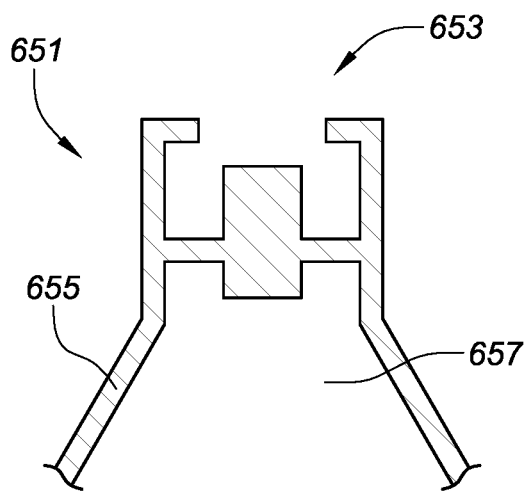
FIGS. 12A and 12B are a cross sectional and top view of an embodiment of a refill bottle that can interact with the eCig tank of FIGS. 11A and 11B to refill the eCig tank.
Figure 12B:
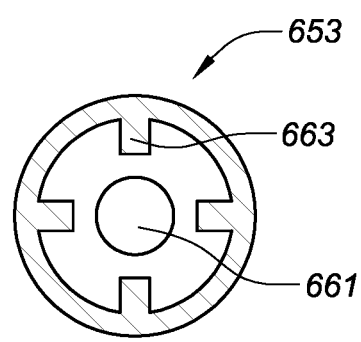

FIGS. 12A and 12B illustrate a cross-sectional view and a top view of another embodiment of a refill bottle 651. The refill bottle can comprise a bottle housing 655, a bottle cavity 657, and a refill assembly 653. The refill assembly 653 can comprise a refill check valve 661 and at least one flange 663. The at least one flange 663 can removably couple with a matching locking interface of an eCig tank. A user can mate the refill assembly 653 with a self-sealing port of an eCig tank and match the at least one flange 663 with a matching interface. The refill check valve 661 can interact with a tank check valve to allow a liquid stored within the bottle cavity 657 to move through the refill check valve 661, through a tank check valve, and into a tank reservoir. When the user has transferred a desired amount of liquid from the refill bottle the user can remove the refill bottle from the tank and reseal the eCig tank and the refill bottle.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

Although at least one embodiment of a device for storing and vaporizing liquid media has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. A refill system for an electronic cigarette, comprising:
a refill bottle comprising a bottle housing, a bottle cavity defined by the bottle housing, and a refill assembly coupled to the bottle housing, the refill assembly comprising a refill check valve, a filling projection, and at least one flange; and
an eCig tank comprising a tank side wall, a tank reservoir defined by the tank side wall, and a self-sealing port coupled to the tank side wall,
wherein the self-sealing port comprises a locking interface, a fill port, and a tank check valve, and wherein the self-sealing port comprises a material that forms the fill port, opens when penetrated by the filling projection, and automatically seals after penetration.

2. The refill system for an electronic cigarette according to claim 1, wherein the material comprises an elastomeric material.

3. The refill system for an electronic cigarette according to claim 2, wherein the elastomeric material comprises a silicone material.

4. The refill system for an electronic cigarette according to claim 1, further comprising a liquid stored within the bottle cavity and wherein the bottle housing is configured to transmit pressure to the bottle cavity such that the applied pressure causes the liquid to move from the bottle cavity, through the refill check valve, and exit the refill bottle.

5. The refill system for an electronic cigarette according to claim 4, wherein the refill check valve is configured to interact with the tank check valve to allow the liquid stored within the bottle cavity to move through the refill check valve, through the tank check valve, and into the tank reservoir.

6. The refill system for an electronic cigarette according to claim 1, wherein the at least one flange is configured to removably couple with the locking interface.

7. A refilling system for an electronic cigarette, comprising:
an electronic cigarette comprising a side wall defining an tank reservoir, and a self-sealing port, wherein the self-sealing port is located on the side wall and comprises a locking interface, a self-sealing port, and a tank check valve, wherein the self-sealing port comprises a material that forms the fill port, opens when penetrated by the filling projection, and automatically seals after penetration; and
a refill bottle, comprising:
a bottle housing;
a bottle cavity defined by the bottle housing; and
a refill assembly comprising a plurality of flanges, the filling projection, and a refill check valve, wherein the plurality of flanges are configured to removably couple with the locking interface of the self-sealing port, and wherein the refill check valve is configured to interact with the tank check valve to allow a liquid stored within the bottle cavity to move through the refill check valve, through the tank check valve, and into the tank reservoir.

8. The refill system for an electronic cigarette according to claim 7, wherein the material comprises an elastomeric material.

9. The refill system for an electronic cigarette according to claim 8, wherein the-elastomeric material comprises a silicone material.

\* \* \* \* \*